United States Patent
Fritz et al.

[11] Patent Number: 5,735,830
[45] Date of Patent: Apr. 7, 1998

[54] POLYMER MATERIAL FOR MEDICAL INSTRUMENTS AND METHOD FOR PRODUCTION OF THE POLYMER MATERIAL

[75] Inventors: Hans-Gerhard Fritz, Uhingen; Rainer Anderlik, Heidelberg; Armin Singvogel, Remseck; Michael Heider, Waiblingen-Neustadt, all of Germany

[73] Assignee: Willy Rüsch AG, Kernen-Rommelshausen, Germany

[21] Appl. No.: 676,356

[22] PCT Filed: Feb. 8, 1995

[86] PCT No.: PCT/DE95/00168

§ 371 Date: Jul. 11, 1996

§ 102(e) Date: Jul. 11, 1996

[87] PCT Pub. No.: WO95/21635

PCT Pub. Date: Aug. 17, 1995

[30] Foreign Application Priority Data

Feb. 9, 1994 [DE] Germany ............... 44 04 041.5

[51] Int. Cl.$^6$ ............................................. A61M 25/00
[52] U.S. Cl. ............... 604/280; 604/264; 525/192; 264/171.23
[58] Field of Search ............... 604/265–266, 604/280, 264; 264/171.23, 171.28, 172.18; 428/423.7, 424.8; 525/191, 192, 194, 193

[56] References Cited

U.S. PATENT DOCUMENTS

| | | | |
|---|---|---|---|
| 4,863,784 | 9/1989 | Lustig et al. | 428/218 |
| 5,288,806 | 2/1994 | Peacock | 525/240 |
| 5,516,845 | 5/1996 | Heese et al. | 525/193 |
| 5,543,223 | 8/1996 | Shah | 428/349 |

FOREIGN PATENT DOCUMENTS

| | | |
|---|---|---|
| 0573884 | 12/1993 | European Pat. Off. |
| 9218173 | 10/1992 | WIPO |

*Primary Examiner*—Michael Powell Buiz
*Assistant Examiner*—Chalin Smith
*Attorney, Agent, or Firm*—Paul J. Vincent

[57] ABSTRACT

A polymer material (6) is formed from a first polyethylene component (1) having a low density (VLDPE) which is silane-grafted with an organic silane (3) in combination with organic peroxide (4) and is cross-linked through storage in a damp environment and/or in water. The polymer material (6) can be processed into medical instruments under dry conditions prior to cross-linkage. After cross-linkage the medical instruments made from the polymer material (6) exhibit a high degree of transparency, are non-buckling and flexible. The polymer material (6) is produced in an extruder, preferentially in a double-worm extruder.

16 Claims, 1 Drawing Sheet

POLYMER MATERIAL FOR MEDICAL INSTRUMENTS AND METHOD FOR PRODUCTION OF THE POLYMER MATERIAL

BACKGROUND OF THE INVENTION

The invention concerns a medical instrument comprising at least one shaft section having a lumen, wherein the shaft section or sections are made from a flexible polymer material.

The invention also concerns a method for the production of a polymer material.

These types of medical instruments, for example, catheters, tubes, tracheal tubes, and the like are, as is known in the art, produced from a plurality of polymer materials. Towards this end, thermoplastics as well as elastomers are utilized. Among the range of thermoplastics, soft PVC materials are still normally used. Due to the low softening temperature of soft PVC materials, sterilization of medical instruments made from this material using hot steam is not possible. Conventional medical instruments made from soft PVC materials can therefore only be used one time in a sterile condition (disposable instruments). As a result, utilization of these medical instruments generates a large number of contaminated instruments which must be disposed of. One disposal possibility is incineration of the contaminated PVC material. Since dioxin is thereby produced, this type of disposal is controversial even when subjected to the most stringent safety conditions.

The PVC polymers which are utilized for medical instruments usually contain softeners for achieving the desired instrument flexibility. The softeners are usually simply physically mixed into the PVC polymer so that it is possible for these materials to diffuse out of the PVC material and into its immediate surroundings. In the event that medical instruments of this type are placed inside humans, it is possible for the softener to enter into the body.

Very-low-density polyethylene (VLDPE) and ultra-low-density polyethylene (ULDPE) are softener-free, soft polymers with characteristic features comparable to soft PVC material and have, as do the soft PVC materials, very low softening temperatures and are therefore not suitable for steam sterilization.

In addition to thermoplastic components such as the kind utilized in medicine, medical instruments are also made from rubber materials which have the advantage, due to their chemical cross-linked structure, of being steam-sterilizable. Rubber materials are non-transparent, require costly processing technology and, compared to thermoplastics, are relatively expensive raw materials.

It is therefore the purpose of the present invention to develop a polymer material for medical instruments which is physiologically unobjectionable, transparent, which can be sterilized by steam, and which has the necessary flexibility while maintaining a constantly open lumen.

It is furthermore the purpose of the present invention to present a method for the production of a polymer material of this type.

SUMMARY OF THE INVENTION

The purpose of the invention is achieved with respect to development of the polymer material in that the polymer material is formed from a first polyethylene component having low density (VLDPE) and/or a second polyethylene component having extreme low density (ULDPE), whereby an organic silane is grafted to the polymer material with the addition of an organic peroxide and the grafted polymer is cross-linked through storage in a humid environment and/or in water.

The above mentioned purpose in accordance with the invention is solved with respect to a method for production of a polymer material of this type in that the first polyethylene component and/or the second polyethylene component are dosed by weight and introduced as pourable bulk material to an extruder, preferably a double-worm extruder, and a mixture comprising organic silane and organic peroxide and, if appropriate, a catalyst is injected into the extruder, preferably using a membrane dosaging pump having a cooled injection valve, and a vacuum for degasing the melt is applied to the extruder in the vicinity of the product discharge with the extruder being heated at least between the region at which the organic silane and the organic peroxide is introduced up to the product discharge and medical instruments are produced from the degased melt of silane-grafted polymer material under dry conditions and subsequently cross-linked by exposure to moisture.

The polymer material in accordance with the invention has the advantage that it has an increased resistance to buckling compared to the initial polymer material. An undesired narrowing of the cross section of the lumen in the event of bending of the medical instrument is opposed by the polymer material itself. In addition, the polymer material in accordance with the invention is free of softeners, surprisingly exhibits the desired transparency and can be steam-sterilized a plurality of times at the medically required temperature of T=134° C. The polymer material in accordance with the invention uses a raw material which is more economical than comparable rubber products and the processing of polymer material in accordance with the invention into medical instruments is possible in a conventional manner under dry conditions.

The processing of the polymer material in accordance with the invention into medical instruments can take place directly after production of the silane-grafted polyethylene melt. The silane-grafting and the extrusion into a tube can also be carried out with an extruder in a single step. The polymer material in accordance with the invention can, however, also be further processed after cooling or after further granulation. In the event that the polymer material in accordance with the invention is stored in a moisture-proof fashion in suitable packaging (for example welded plastic bags), it can still easily be further processed following storage times of several weeks.

The method in accordance with the invention facilitates the production of the silane-grafted polymer melt in an economical and reproducible fashion using simple processing steps. The reacting chemicals are homogeneously distributed in the first and/or second polyethylene components using conventional and reliable machine technology so that one obtains an end product which is free of gel particles and pinholes.

If, in a preferred embodiment of the invention, a catalyst or a catalyst mixture is added to the polymer material the cross-linking time can be precisely determined. The processing time is likewise shortened, for example the time for the welding of components. Dibutyltindilaurate (DBTL) and/or a titanylacetonate are particularly well suited as catalysts. A mixture of a plurality of suitable chemicals can also be utilized as a catalyst.

In a further embodiment of the invention, the first polyethylene component and/or the second polyethylene component have a narrow molecular mass distribution. The molar mass distribution lies in the range of $1.5 \leq \overline{M}_w/\overline{M}_n \leq 3.0$. Thereby $\overline{M}_w$ respresents the weight-averaged molecular weight and $\overline{M}_n$ the number-averaged molecular weight of the polyethylene components. The ratio of $\overline{M}_w$ to $\overline{M}_n$ as formulated in patent claim 4 characterizes the width of the molecular weight distribution. It is preferred in accordance with the invention to choose a polyethylene component or polyethylene component mixture having a ratio $\overline{M}_w/\overline{M}_n$ of 2. This type of molar mass distribution facilitates a surprisingly high gel-content in the vicinity of $65\% \leq C_G \leq 95\%$ which cannot be achieved with conventional VLDPE and also a high degree of cross-linking in the end product, a high degree of cross-linking being a requirement for steam-sterilizability.

A further embodiment of the invention utilizes an organic peroxide whose decomposition temperature region lies above the melt temperature of the first polyethylene component and/or of the second polyethylene component. Dicumylperoxide (DCUP), Dibenzoylperoxide (DB) and/or dimethylhexanebutylperoxide (DHBP) are preferentially utilized as organic peroxides. The organic silane utilized is added to the polyethylene component or components in weight ranges of 0.5 to 5% by weight and the organic peroxide in the range between 0.02 to 0.3% by weight.

Dibutyltindilaurate (DBTL) in the range from 0 to 0.05% by weight or titanylacetonate in the range from 0 to 0.5% by weight is added as catalyst to the polymer material in accordance with the invention.

A functional polymer material can be obtained from a flexible polyethylene material of low or extremely low density using the smallest fractions of reaction chemicals and can be processed under dry conditions into medical components, as can all thermoplastics, using extrusion, injection moulding, inflation techniques and welding.

In a preferred embodiment of the method the first polyethylene component and/or the second polyethylene component is mixed with the reaction chemicals at ambient temperature in a mixing apparatus prior to the introduction into the extruder and the bulk material, water-blown by the reaction chemicals, is subsequently introduced to the reaction extruder. This type of processing procedure results in a very homogeneous raw material which, if appropriate, can also be processed in a single-worm extruder into polymer material in accordance with the invention.

In further embodiments of the invention the water cross-linking of the medical instruments produced from the polymer material in accordance with the invention is carried out at a temperature level which lies below the softening temperature of the original polyethylene materials until the shape of the instrument is stabilized by the silane cross-linking reactions. After this forming or shape-fixing, the temperature of the cross-linking bath can be increased until complete cross-linking occurs. In this fashion the time needed for complete cross-linking of the polymer material is reduced.

In a further embodiment of the invention the medical instrument is produced from a silane-grafted polymer material which is cross-linked in a shaping tool.

In a preferred embodiment thereof, the silane-grafted polymer material is also pressed into moulded extrusions, such as, for example, tubes. The moulded extrusion is subsequently introduced to a shaping tool and the tool containing the moulded extrusion is brought into a water bath.

The ultra-low or very-low-density polyethylene (ULDPE), VLDPE) are normally pressed into moulded extrusions in a single step process which includes the silane-grafting and shaping. This type of moulded extrusions (intermediate product), which have a gel-content <5% at the output of the nozzle, are subsequently introduced to a shaping tool. In the event that a medical instrument is to be manufactured from the intermediate product, a processing of the intermediate product into the desired instrument must take place prior to the shaping and cross-linking step. Subsequent thereto the shaping tool having the intermediate product or the completed instrument is introduced into a water bath. Cross-linking reactions form a three-dimensional cross-linked structure from the partial product (extrusion) in dependence on the susceptibility to grafting, water temperature, and cross-linking time. The cross-linking of the macromolecules takes place by means of Si—O—Si bridges. The formed cross-linkage fixes the geometry of the extrusion which pervades the intermediate product during the cross-linking phase.

When, after completion of the cross-linking reaction, the formed component is removed from the forming tool, the geometry of the formed component is maintained. This geometry is rigidly formed through the macromolecular cross-linkage and is maintained even under the influence of steam sterilization. This is a substantial advantage relative to medical instruments made from PVC.

The polymer material in accordance with the invention and a method for production of this material are described and explained more closely below in connection with the embodiments represented in the drawings. The features which can be extracted from the description and the drawing can be used in other embodiments of the invention individually or collectively in arbitrary combination.

DESCRIPTION OF THE PREFERRED EMBODIMENT

Figure 1:
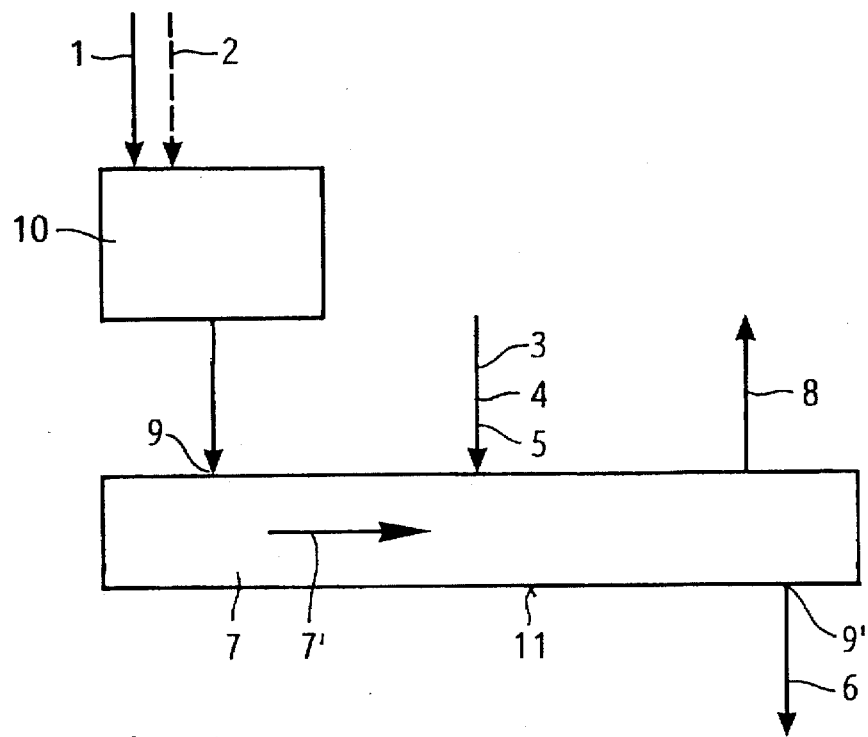
FIG. 1 shows a flow diagram for the production of the polymer material in accordance with the invention.

A first polyethylene component 1 or a second polyethylene component 2 either alone or in mixture with an organic silane 3 and a peroxide 4 as well as, if appropriate, a catalyst 5, are thoroughly mixed and subjected to an increased temperature in the range between $140° \leq T \leq 200°$ C. This type of heat treatment leads to the formation of silane-grafted polymer material 6, which can be further processed in the manner of conventional thermoplastics under dry conditions. For example, this heat treatment can occur in an extruder 7. The first polyethylene component 1 or the second polyethylene component 2 or a mixture of polyethylene components travel through the extruder 7 in the direction 7' of material flow. A vacuum 8 is applied in the end region of the extruder 7 to effect degasing of the melt. The first and/or second polyethylene components 1, 2 flow into the extruder 7 in a continuous fashion at the product input 9. The input product passes, prior to entrance into the extruder 7, through a dosing unit 10, for example a differential dosaging scale, and is admeasured by weight. The silane-grafted polymer material 6 leaves the extruder 7 via the product discharge 9' and is subsequently granulated according to a conventional method. The extruder 7 has a heater 11 for heat-treating the polyethylene granulate and the reaction mixture.

The first and/or second polyethylene components 1, 2 having very low density (for example VLDPE, ULDPE) can be produced with special polymerization procedures, for example, by "constraint geometry catalyst technology". These polyethylene components having, preferentially, a narrow molar mass distribution ($1.5 \leq M_w/M_n \leq 3.0$, preferentially approximately 2.0) are, for example, silane-grafted in a double-worm extruder through the addition of an organic silane/peroxide mixture. A uni-directionally rotating, densely-combing extruder 7 (double-worm extruder) is particularly well suited for this purpose, since it has high mixing and homogenizing efficiency.

In accordance with FIG. 1, the dosing unit 10 transports either the first polyethylene component 1 or the second polyethylene component 2 or, for example, a mixture of the above polyethylene components in granulated form into the extruder 7. After the first polyethylene component 1 has been melted, a mixture comprising organic silane 3 and peroxide 4 and, if appropriate, also a catalyst 5 is injected downstream into the extruder 7 by means of a membrane dosaging pump and a cooled injection valve. At this location the reaction fluid is thoroughly mixed with the first polyethylene component 1 at a reduced temperature ($90°\ C. \leq T_M \leq 130°\ C.$) prior to reactive decomposition of the peroxide 4 due to further temperature increase along the extruder 7. The organic silane molecules become coupled to radicals produced in the polymer chain or polymer chains by the decay of the organic peroxide 4. Appropriate organic peroxides are, for example, dimethylhexanebutylperoxide (DHBP), dicumylperoxide (DCUP), dibenzoylperoxide (DB) or other peroxide types with which decomposition occurs above the melting temperature of the first polyethylene component 1. Organic silanes 3 which are particularly well suited are those with which the Si-atoms are joined with alkoxy-groups. Vinyltrimethoxysilane (VTMOS) and vinyltriethoxysilane (VTEOS) are preferentially utilized here. In addition, catalysts 5 (cross-linking catalysts) such as dibutyltindilaurate (DBTL) or titanylacetonate as well as additional catalysts which enhance the hydrolysis and condensation reaction of the organic silanes can be added to the reaction mixture comprising peroxide 4 and organic silane 3. A silane-grafted polymer material 6 having an output gel-content of 0% is available after degasing of the melt from which medical instruments can be produced using conventional methods of thermoplastic processing. The processing of the silane-grafted polymer material can be carried out directly or subsequent to a cooling and granulating step.

Since, in contrast to conventional methods for rubber processing, silane cross-linking systems are not formed by a temperature increase rather through the exposure of the medical instrument to a moist environment or through storage in water, the storage conditions determine the point in time at which the cross-linking begins and thereby the amount of time available for processing and packaging of the silane-grafted polymer material. The cross-linking reactions can also be accelerated by storing the components made from the polymer material 6 in water at elevated temperatures. The water bath temperature must however not exceed the softening temperature or the crystallite melt temperature of the polymer material ($60° \leq T_e \leq 72°\ C.$). Only after the cross-linking reactions have fixed the shape of the medical instrument, can the water bath temperature exceed the softening temperature of the raw material (untreated material) to shorten the time for complete cross-linking of the polymer material.

In addition to the receptivity, i.e. the organic silane, peroxide, and catalyst components, the quality of the silane-grafted polymer material is substantially determined by the homogeneity of the mixing of these reaction chemicals in the polymer melt. An inhomogeneous distribution of the reaction chemicals can lead to quality-reducing pinholes and gel particles in the polymer material.

Figure 2:
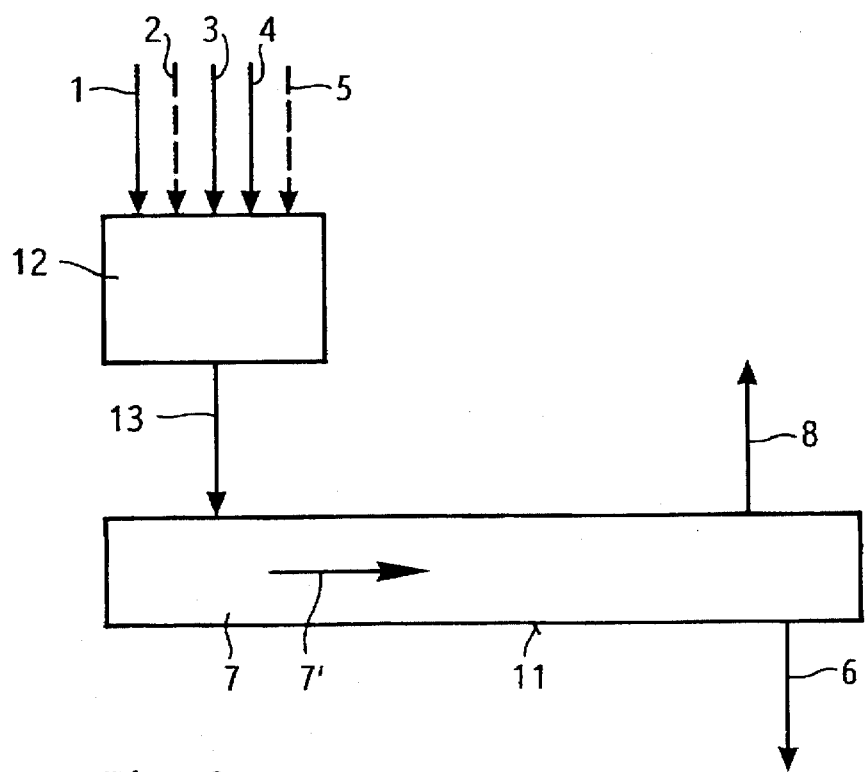
FIG. 2 shows a further alternative flow diagram for facilitating the manufacture of the polymer material in accordance with the invention.

FIG. 2 shows a mixer 12, preferentially operating in batch-mode, into which the first polyethylene component 1 or alternatively a second polyethylene component 2, an organic silane 3, a peroxide 4, and, if appropriate, a catalyst 5, i.e. a liquid grafting receptor, are introduced. Both, the first polyethylene component 1 as well as the second polyethylene component 2 can be prewarmed. These components are homogeneously mixed together in the mixer 12 until the fluid has completely diffused into the first polyethylene granular component 1. In this manner, an exceptionally good predistribution of the grafting receptors results within the polyethylene matrix. Local cross-linked clusters and pinholes are avoided. The improved predistribution allows for equal gel-content with a reduced amount of grafting receptor. Subsequent thereto, the bulk material mixture 3, water-blown with reaction chemicals, is admeasured into the extruder 7, where the silane grafting reaction occurs. The homogeneous premixing allows for, in the method variation represented in FIG. 2, in addition to the conventional double-worm extruder also the utilization of a more economical single-worm extruder having mixing elements. The material flow is indicated by 7' in FIG. 2 and a degasing of the melt is effected by the applied vacuum 8. The silane-grafted polymer material 6 leaves the extruder 7 at the end region.

Both method variations shown in FIGS. 1 and 2 are operated continuously.

EXAMPLES

The silane-grafted polymer materials I through IV whose composition is given in table 1 were produced according to the production variations indicated in FIG. 1 or FIG. 2.

| | Polymer material I | Polymer material II | Polymer material III | Polymer material IV |
|---|---|---|---|---|
| Polyethlene componente "Exact" Manufacturer: Exxon Chemicals | 100 | 100 | 100 | 100 |
| VTEOS (Organic silane) | 2,5 | — | — | — |
| VTMOS (Organic silane) | — | 2,5 | 2,5 | 2,5 |
| DHBP (Peroxide) | 0,08 | 0,08 | 0,08 | 0,08 |
| DBTL (Catalyst) | | | 0,02 | |
| Titanylacetonate (Catalyst) | | | | 0,1 |

After the ULDPE polyethylene component is admeasured into the extruder via a funnel and melted, the mixture of liquid reaction chemicals (organic silane, peroxide, and, if appropriate, catalyst) is pumped into the extruder via a diaphragm dosing pump. The silane-grafting reaction occurs therein. The polymer material leaving the extruder is cooled, and, for example, granulated. The polymer granulate produced from the polymer material is subsequently processed under dry conditions by means of an additional extruder into, for example, tubes. A comparison between materials I and II has shown that the cross-linking reaction occurs significantly faster when utilizing VTMOS compared to VTEOS. In the event that the silane-grafted polymer materials I and II are welded in suitable plastic bags in a moisture-tight fashion, both materials remain processable even after several weeks of storage. In damp environments or in water, the hydrolysis and condensation reactions occur significantly faster with VTMOS than with VTEOS. In addition, the cross-linking reaction can be increased through the addition of a "master batch" in a tube extrusion process. The "master batch" contains either the catalyst DBTL or titanylacetonate. In the event that the catalyst is already present in the polymer material due to the preparation procedure, the available packaging time, for example that for the welding of components, is reduced as is the cross-linking time in the water bath or in the moist atmosphere.

The cross-linked tubes made from materials I through III are as transparent as tubes made from non-cross-linked ULDPE. The cross-linked tubes made from materials I through III can be easily steam-sterilized at a temperature of T=134° C. The resistance to buckling of the tubes made from materials I through III is likewise substantially improved relative to the non-cross-linked raw materials. In experiment IV (polymer material IV) a bulk material mixture is produced prior to the extrusion process and the polyethylene components are mixed with the liquid reaction chemicals until same completely diffuse into the polyethylene components. The bulk material mixture was subsequently admeasured into the double-worm extruder. The polymer material IV is a silane-grafted material having few pinholes and gel particles (high product quality). The polymer material IV exhibits a transparency comparable to that of polymer materials I through III. Polymer material IV can be steam-sterilized and is non-buckling. In this manner, the polymer material IV exhibits the same positive product characteristics as the polymer materials I through III.

A polymer material 6 is formed from a first polyethylene component 1 having a low density (VLDPE) which is silane-grafted with an organic silane 3 in combination with organic peroxide 4 and is cross-linked through storage in a damp environment and/or in water. The polymer material 6 can be processed into medical instruments under dry conditions prior to cross-linkage. After cross-linkage the medical instruments made from the polymer material 6 exhibit a high degree of transparency, are non-buckling and flexible. The polymer material 6 is produced in an extruder, preferentially in a double-worm extruder.

We claim:

1. A medical instrument comprising:
    a shaft section having a lumen and formed from a flexible polymer, said flexible polymer comprising at least one of a very low density polyethylene component (VLDPE) and an ultra low density polyethylene component (ULDPE), said flexible polymer being silane-grafted with an organic silane and organic peroxide and being cross-linked by exposure to a water environment.
2. The instrument of claim 1, wherein said flexible polymer comprise 0.5 to 5% by weight of organic silane and 0.02 to 0.3% by weight of organic peroxide.
3. The instrument of claim 1, wherein said flexible polymer has a gel-content $C_G$ of $65\% \leq C_G \leq 95\%$.
4. The instrument of claim 1, wherein said flexible polymer is cross-linked in a molding tool or unit.
5. The instrument of claim 1, wherein said very and said ultra low components have a narrow molar mass distribution.
6. The instrument of claim 5, wherein said mass distribution is in the range $1.5 \leq \overline{M}_w/\overline{M}_n \leq 3.0$, $\overline{M}_w$ being a weight-averaged and $\overline{M}_n$ a number-averaged molecular weight of said components.
7. The instrument of claim 1, wherein said organic peroxide has a decomposition temperature above a melting temperature of the very low and ultra low components.
8. The instrument of claim 7, wherein said organic peroxide comprises at least one of dicumylperoxide (DCUP), dibenzoylperoxide (DB) and dimethylhexanebutylperoxide (DHBP).
9. The instrument of claim 1, wherein a catalyst is added to the flexible polymer.
10. The instrument of claim 9, wherein said catalyst comprises at least one of dibutyltindilaurate (DBTL) and titanylacetonate.
11. The instrument of claim 10, wherein said dibutyltindilaurate is in a range less than 0.05% by weight and said titanylacetonate is in a range less than 0.5% by weight.
12. Method for producing a medical instrument, the instrument having a shaft section with a lumen therein, the shaft section formed from a flexible polymer, the method comprising the steps of:
    dosing by weight at least one of a first and a second polyethylene component;
    introducing said first and second components as pourable bulk material to an extruder;
    mixing said bulk material with organic silane and organic peroxide;
    applying vacuum to said extruder in a product discharge region to devolatilize a melt;
    heating said extruder from a region of input of said organic silane and said organic peroxide to said product discharge region;
    producing medical instruments from devolatilized silane-grafted polymer; and
    cross-linking said medical instruments through introduction of moisture.
13. The method of claim 12, wherein said extruder is a twin screw extruder and said mixing step comprises injection of a catalyst, said silane, and said peroxide downstream into said extruder using a diaphragm dosing pump having a cooled injection valve.
14. The method of claim 12, wherein said mixing step comprises mixing at least one of said first and said second polyethylene components with said organic silane and said organic peroxide at ambient temperature in a closed mixer prior to introduction to said extruder.
15. The method of claim 12, wherein said cross-linking step is carried out at a first temperature below a softening temperature of said first and said second component to stabilize a shape of the medical instrument and further comprising the step of increasing said first temperature after said shape is stabilized.
16. The method of claim 12, wherein said producing step comprises extrusion of silane-grafted polymer into an extrudate, and introducing this extrudate into a shaping tool, and said cross-linking step comprises introducing said shaping tool containing said extrudate into a water bath.

* * * * *